(12) United States Patent
Wang et al.

(10) Patent No.: US 11,026,581 B2
(45) Date of Patent: Jun. 8, 2021

(54) OPTICAL PROBE FOR DETECTING BIOLOGICAL TISSUE

(71) Applicant: INDUSTRIAL TECHNOLOGY RESEARCH INSTITUTE, Hsinchu (TW)

(72) Inventors: Chy-Lin Wang, Zhudong Township, Hsinchu County (TW); Yuan-Chin Lee, Hsinchu (TW); Chun-Chieh Huang, Hsinchu (TW); Hung-Chih Chiang, Chiayi (TW); Chih-Ming Cheng, Fuxing Township, Changhua County (TW); Shuen-Chen Chen, Taichung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 479 days.

(21) Appl. No.: 15/717,116

(22) Filed: Sep. 27, 2017

(65) Prior Publication Data
US 2018/0092539 A1     Apr. 5, 2018

Related U.S. Application Data

(60) Provisional application No. 62/401,947, filed on Sep. 30, 2016.

(30) Foreign Application Priority Data

Sep. 12, 2017   (TW) .................................. 106131131

(51) Int. Cl.
*A61B 5/00*     (2006.01)
*A61B 1/04*     (2006.01)

(52) U.S. Cl.
CPC .......... *A61B 5/0066* (2013.01); *A61B 5/0064* (2013.01); *A61B 1/043* (2013.01);
(Continued)

(58) Field of Classification Search
CPC ..... A61B 5/0066; A61B 5/0064; A61B 1/043; A61B 5/0071; A61B 5/0073;
(Continued)

(56) References Cited

U.S. PATENT DOCUMENTS 5,788,639 A   8/1998  Zavislan et al.
7,460,248 B2  12/2008 Kurtz et al.
(Continued)

FOREIGN PATENT DOCUMENTS

CN    1911158 A     2/2007
CN  101652784 A     2/2010
(Continued)

OTHER PUBLICATIONS

Taniguchi, K. "A tutorial for designing fundamental imaging systems." University of Arizona OPTI 521 Tutorial. Nov. 2009.*
(Continued)

*Primary Examiner* — Pascal M Bui Pho
*Assistant Examiner* — Amal Aly Farag
(74) *Attorney, Agent, or Firm* — Muncy, Geissler, Olds and Lowe, P.C.

(57) ABSTRACT

An optical probe for detecting a biological tissue includes a surface imaging module and a tomography capturing module. The surface imaging module captures and creates a surface image of the biological tissue, and at least includes a light source emitting a first detecting light. The tomography capturing module captures a tomography image of the biological tissue and receives a second detecting light. The first detecting light passes via a first optical path from the light source to an imaging sensor through the biological (Continued)

tissue, a telecentric lens, a first optical mirror, and a lens assembly in sequence. The second detecting light passes via a second optical path from a first collimator to the first collimator through a scanner, the first optical mirror, the telecentric lens, the biological tissue, the telecentric lens, the first optical mirror, the scanner, and the first collimator in sequence.

18 Claims, 5 Drawing Sheets

(52) U.S. Cl.
CPC .......... *A61B 5/0071* (2013.01); *A61B 5/0073* (2013.01); *A61B 5/0082* (2013.01)

(58) Field of Classification Search
CPC ..... A61B 5/0082; A61B 5/0075; A61B 5/441; A61B 5/443; A61B 3/102; A61B 2090/3735; A61B 8/4444; A61B 2017/320073
See application file for complete search history.

(56) References Cited

U.S. PATENT DOCUMENTS

| | | | |
|---|---|---|---|
| 7,859,682 B2 | 12/2010 | Smith et al. | |
| 7,918,791 B2 | 4/2011 | Lu et al. | |
| 8,873,034 B2 | 10/2014 | Lin et al. | |
| 2006/0063986 A1 | 3/2006 | Hogan | |
| 2006/0119858 A1* | 6/2006 | Knighton | G01B 9/02091 356/479 |
| 2007/0263226 A1* | 11/2007 | Kurtz | A61B 5/0059 356/492 |
| 2010/0321700 A1 | 12/2010 | Hirose et al. | |
| 2011/0164220 A1* | 7/2011 | Su | G01J 1/0414 351/221 |
| 2011/0206254 A1* | 8/2011 | Patwardhan | A61B 5/0077 382/128 |
| 2011/0273757 A1* | 11/2011 | Kobayashi | A61B 3/102 359/204.2 |
| 2012/0188538 A1* | 7/2012 | Patil | A61B 3/102 356/301 |
| 2012/0281071 A1* | 11/2012 | Bergman | G01B 11/25 348/46 |
| 2013/0169931 A1 | 7/2013 | Lee et al. | |
| 2013/0182096 A1 | 7/2013 | Boccara et al. | |
| 2013/0242311 A1* | 9/2013 | Usami | G01B 9/02007 356/492 |
| 2014/0218740 A1 | 8/2014 | Nebosis et al. | |
| 2015/0043003 A1* | 2/2015 | Chung | A61B 3/102 356/479 |
| 2017/0193659 A1 | 7/2017 | Wang et al. | |

FOREIGN PATENT DOCUMENTS

| | | |
|---|---|---|
| CN | 102670177 A | 9/2012 |
| CN | 103181746 A | 7/2013 |
| CN | 104352216 A | 2/2015 |
| CN | 204694910 U | 10/2015 |
| CN | 105725979 A | 7/2016 |
| CN | 10703706 A | 8/2017 |
| TW | I342201 B | 5/2011 |
| TW | I385598 B | 2/2013 |
| TW | I513450 B | 12/2015 |
| TW | I519277 B | 2/2016 |
| WO | WO 02/059643 A2 | 8/2002 |

OTHER PUBLICATIONS

Chien-Chung Tsai, et al., "Full-depth epidermis tomography using a Mirau-based full-field optical coherence Tomography", Biomedical Optics Express, Sep. 1, 2014, vol. 5, No. 9, pp. 3001-3010.
J. Kraute, et al., "Optical design of a Vertically Integrated Array-type Mirau-based OCT System", Proc. of SPIE, 2014, vol. 9132, pp. 91320L-1-91320L-7.
Alex Zlotnik, et al., "Improved extended depth of focus full field spectral domain Optical Coherence Tomography", Optics Communications, 2010, vol. 283, Iss. 24, pp. 4963-4968.
Seungwan Lee, et al., "Optical probe design with extended depth-of-focus for optical coherence microscopy and optical coherence tomography", Proc. of SPIE, 2013, vol. 8616, pp. 861604-1-861604-8.
Joseph A. Izatt, et al., "Optical coherence microscopy in scattering media", Optics Letters, vol. 19, No. 8, Apr. 15, 1994, pp. 590-592.
Maciej Wojtkowski, et al., "In vivo human retinal imaging by Fourier domain optical coherence tomography", Journal of Biomedical Optics, Jul. 2002, vol. 7, No. 3, pp. 457-463.
Arnaud Dubois, et al., "High-resolution full-field optical coherence tomography with a Linnik microscope", Applied Optics, Feb. 1, 2002, vol. 41, No. 4, pp. 805-812.
M. Wojtkowski, et al., "Full range complex spectral optical coherence tomography technique in eye imaging", Optics Letters, Aug. 15, 2002, vol. 27, No. 16, pp. 1415-1417.
Yong Huang, et al., "Motion-compensated hand-held common-path Fourier-domain optical coherence tomography probe for image-guided intervention", Biomedical Optics Express , Dec. 1, 2012, vol. 3, No. 12, pp. 3105-3118.
Boris Považay, et al., "Full-field time-encoded frequency-domain optical coherence tomography", Optics Express, Aug. 21, 2006, vol. 14, No. 17, pp. 7661-7669.

* cited by examiner

OPTICAL PROBE FOR DETECTING BIOLOGICAL TISSUE

CROSS-REFERENCE TO RELATED APPLICATION

This application claims the priority benefits of U.S. Provisional Application No. 62/401,947, filed on Sep. 30, 2016 and Taiwan Application No. 106131131, filed on Sep. 12, 2017. The entirety of each of the above-mentioned patent applications is hereby incorporated by reference herein.

TECHNICAL FIELD

The technical field relates to an optical probe for detecting biological tissue.

BACKGROUND

A commercial dermoscopy is used to detect only surface of skin, such as all kinds of freckles, wrinkles, pores, rough degrees of skin, degrees of dull skin, acne, and pocks, but the commercial dermoscopy cannot detect a deep structure of skin to obtain important characteristics which is used to determine whether an appearance is ageing or not, such as thickness of epidermis, thickness of dermis, density of collagen, density of elastic fiber, structures of pores, secretory capacity of sebaceous gland, and forms of blood vessels. As a result, the commercial dermoscopy cannot early monitor the symptom of early aging for correct anti-aging treatment.

A common optical coherence tomography (OCT) imaging system of skin is used to detect deep structures of skin, such as thickness of epidermis, thickness of dermis, density of collagen, density of elastic fiber, structures of pores, secretory capacity of sebaceous gland, and forms of blood vessels, but the common optical coherence tomography imaging system cannot obtain surface images of skin, such as all kinds of freckles, wrinkles, pores, rough degrees of skin, degrees of dull skin, acne, and pocks. As a result, there exists lots of blind spots for detecting, so that it is hard to evaluate appropriate and correct anti-aging treatment.

SUMMARY

According to an embodiment of the disclosure, an optical probe for detecting a biological tissue includes a surface imaging module capturing a surface image of the biological tissue, wherein the surface imaging module includes a telecentric lens, a first optical mirror, a lens assembly, an imaging sensor, and a light source emitting a first detecting light; and a tomography capturing module, capturing a tomography image of the biological tissue and receiving a second detecting light, wherein the tomography capturing module includes the telecentric lens, the first optical mirror, a scanner, and a first collimator, wherein the first detecting light passes via a first optical path from the light source to the imaging sensor through the biological tissue, the telecentric lens, the first optical mirror, and the lens assembly in sequence, and the second detecting light passes via a second optical path from the first collimator to the first collimator through the scanner, the first optical mirror, the telecentric lens, the biological tissue, the telecentric lens, the first optical mirror, the scanner, and the first collimator in sequence.

The foregoing will become better understood from a careful reading of a detailed description provided herein below with appropriate reference to the accompanying drawings.

DETAILED DESCRIPTION OF DISCLOSED EMBODIMENTS

Figure 1:
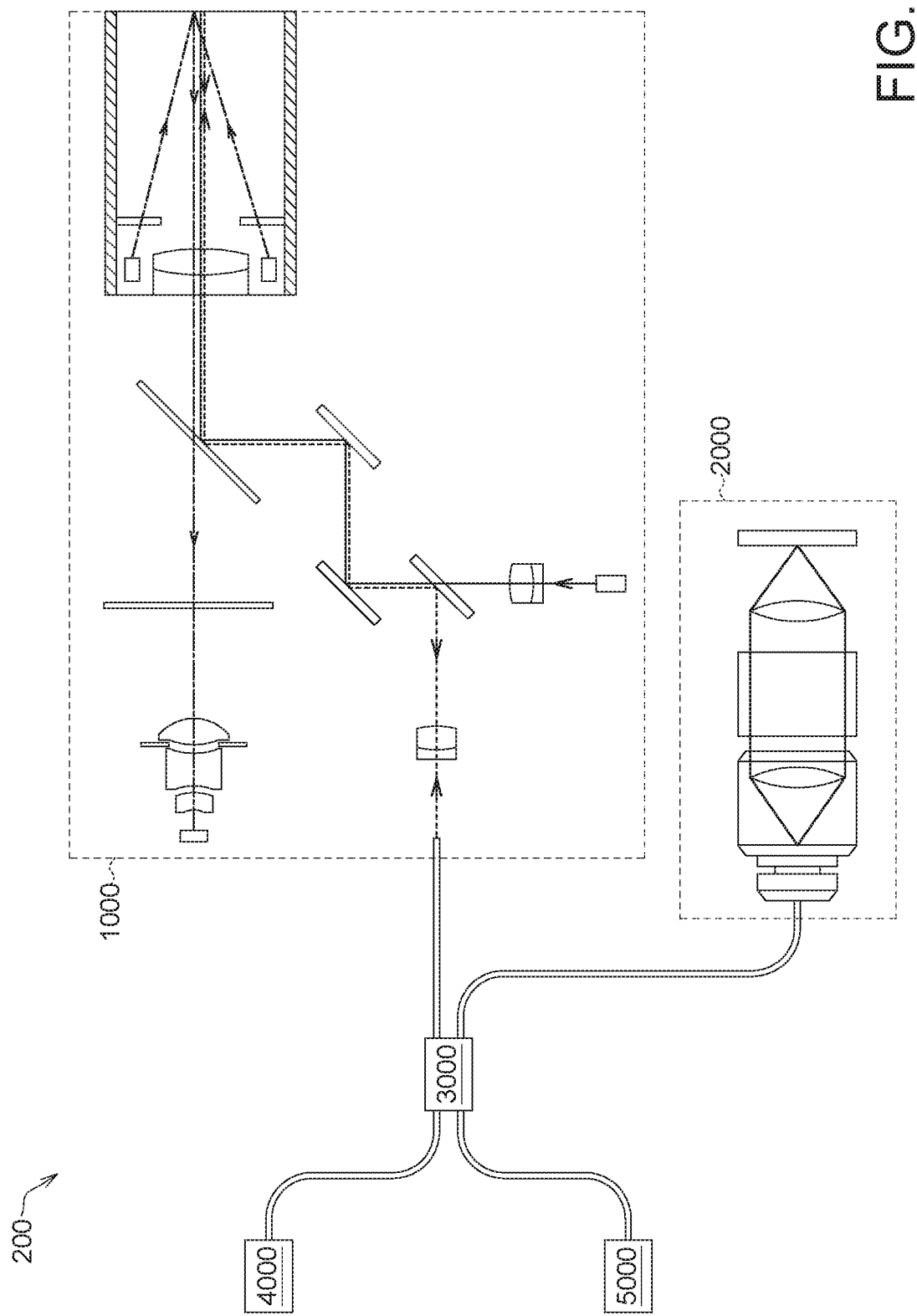
FIG. 1 is a schematic diagram of an optical probe for detecting a biological tissue, which is applied to an optical detecting system, according to an exemplary embodiment of the disclosure.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

According to an embodiment of the disclosure, an optical probe for detecting a biological tissue may capture a surface image and a tomography image of the biological tissue, and couple to an image process system to detect a skin layer and a deep layer status at the same time.

As shown in FIG. 1, an optical detecting system 200 may be an optical coherence tomography (OCT) system. In the embodiment of the disclosure, an optical probe 1000 for detecting a biological tissue couples to an optical fiber coupler 3000. The optical fiber coupler 3000 receives a light beam emitted from a broad band light source 4000 and separates the light beam to a sample beam and a reference beam. The optical probe 1000 for detecting the biological tissue is used as a sample arm of the OCT system and receives the sample beam from the optical fiber coupler 3000. The sample beam reflected from the biological tissue and the reference beam came from a reference arm 2000 form an interference signal, and the interference signal is analyzed and processed in a tomography analysis module 5000 to form a tomography image of the biological tissue.

Figure 2:
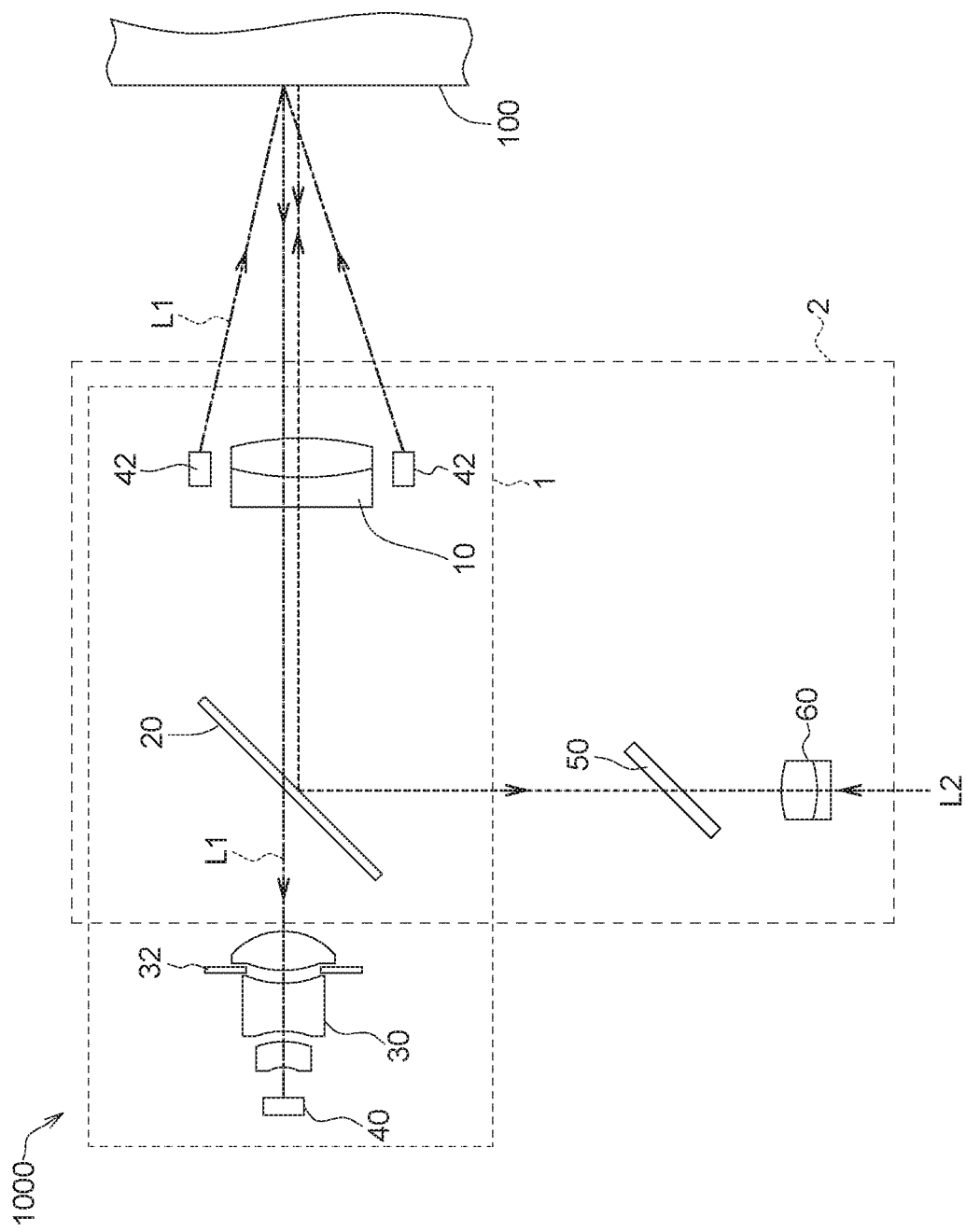
FIG. 2 is a schematic diagram of an optical probe for detecting a biological tissue according to an exemplary embodiment of the disclosure.

With referring to FIG. 2, an optical probe 1000 for detecting a biological tissue 100 includes a surface imaging module 1 capturing a surface image of the biological tissue 100, wherein the surface imaging module 1 includes a telecentric lens 10, a first optical mirror 20, a lens assembly 30, an imaging sensor 40, and a light source 42 emitting a first detecting light L1; and a tomography capturing module 2, capturing a tomography image of the biological tissue 100 and receiving a second detecting light L2, wherein the tomography capturing module includes the telecentric lens 10, the first optical mirror 20, a scanner 50, and a first collimator 60, wherein the first detecting light L1 passes via a first optical path from the light source 42 to the imaging sensor 40 through the biological tissue 100, the telecentric lens 10, the first optical mirror 20, and the lens assembly 30 in sequence, and the second detecting light L2 passes via a second optical path from the first collimator 60 to the first collimator 60 through the scanner 50, the first optical mirror 20, the telecentric lens 10, the biological tissue 100, the telecentric lens 10, the first optical mirror 20, the scanner 50, and the first collimator 60 in sequence.

In the embodiment of the disclosure, a skin tissue is taken as an example, but the scope of the disclosure is not limited thereto. The surface imaging module 1 of the optical probe 1000 for detecting the biological tissue 100 may capture a surface image of skin for determining tissue structures of a skin layer. The tomography capturing module 2 of the optical probe 1000 for detecting the biological tissue 100 may capture a tomography image of skin for obtaining tissue structures of a deep layer. The surface imaging module 1 and the tomography capturing module 2 share the telecentric lens 10 and the first optical mirror 20, so the telecentric lens 10 and the first optical mirror 20 need to be carefully designed to make the surface imaging module 1 and the tomography capturing module 2 workable.

Figure 3:
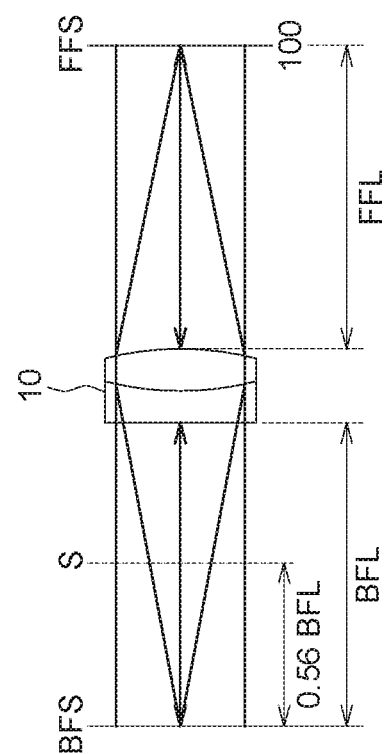
FIG. 3 is a schematic diagram of focal planes of a telecentric lens of an optical probe for detecting a biological tissue according to an exemplary embodiment of the disclosure.

Please refer to FIG. 2 and FIG. 3. In the embodiment, a focal length of the telecentric lens 10 ranges from 25 mm to 40 mm, and the biological tissue 100 is located on a front focal plane FFS of the telecentric lens 10 during the detecting process. If the focal length of the telecentric lens 10 is designed to be longer than the range of 25 mm to 40 mm, a request of a diameter of the lens assembly 30 will increase so that there are not enough space to dispose the lens assembly 30 in the optical probe 1000 for detecting the biological tissue 100. In addition, a f-number (F/#) of the surface imaging module 1 is too large so that the imaging sensor 40 is underexposed, and the optical probe 1000 for detecting the biological tissue 100 needs to dispose the light source 42 with higher light intensity, thereby resulting in power consumption. However, if the focal length of the telecentric lens 10 is shorter than the range of 25 mm to 40 mm, there are not enough space to dispose related elements. In one embodiment, the focal length of the telecentric lens 10 is longer than a focal length of the lens assembly 30. More specifically, a ratio of the focal length of the telecentric lens 10-to the focal length of the lens assembly 30 ranges from 1.4 to 2.8.

Firstly, the surface imaging module 1 is described. In the embodiment of FIG. 2, the telecentric lens 10 is disposed between the first optical mirror 20 and the biological tissue 100. The lens assembly 30 is disposed at one side of the first optical mirror 20 opposite to the telecentric lens 10, and the lens assembly 30 is disposed between the imaging sensor 40 and the first optical mirror 20. The first detecting light L1 emitted from the light source 42 radiates towards the biological tissue 100, then the first detecting light L1 scattered and reflected by the biological tissue 100 goes back to the telecentric lens 10 via the first light path, and enters the lens assembly 30 by the guiding of the first optical mirror 20. In one embodiment, the lens assembly 30 may include at least two lens made from glass or plastic. The first detecting light L1 is focused by the lens assembly 30 and then passed to the imaging sensor 40 to form the surface image of the biological tissue 100.

Please refer to FIG. 1 and FIG. 2. The tomography capturing module 2 is described. In the embodiment of FIG. 2, the scanner 50 is disposed between the first optical mirror 20 and the first collimator 60. Besides, the scanner 50 is not disposed in a connection line of the telecentric lens 10 and the lens assembly 30, but disposed in a projection position of the first optical mirror 20. The second detecting light L2 (sample beam) received by the tomography capturing module 2 is collimated by the first collimator 60, then enters the scanner 50 to scan via the second optical path. The first optical mirror 20 guides the second detecting light L2 to the telecentric lens 10 and the biological tissue 100. Then, the second detecting light L2 reflected by the biological tissue 100 enters the scanner 50 and the first collimator 60, from the telecentric lens 10 through the first optical mirror 20. Next, the optical fiber coupler 3000 coupled to the tomography capturing module 2 receives the second detecting light L2 and the reference beam passed from the reference arm 2000 and forms the interference signal. Finally, the interference signal is sent to the tomography analysis module 5000 to analysis and process, and then form the tomography image of the biological tissue 100.

The first optical mirror 20 guides the first detecting light L1 and the second detecting light L2. The first optical mirror 20 may be a dichroic mirror to allow an incident light with a specific wavelength range passing through, and to reflect another incident light with other wavelength ranges. In the embodiment of FIG. 2, the first optical mirror 20 may have the first detecting light L1 penetrating and may have the second detecting light L2 being reflected. In detail, the first optical mirror 20 can may be designed to allow a light with a wavelength ranging from 300 nm to 700 nm passing through, and to allow a light with a wavelength ranging from 700 nm to 900 nm being reflected. Therefore, the wavelength corresponding to the first detecting light L1 will range from 300 nm to 700 nm, and the wavelength corresponding to the second detecting light L2 will range from 700 nm to 900 nm.

Figure 4:
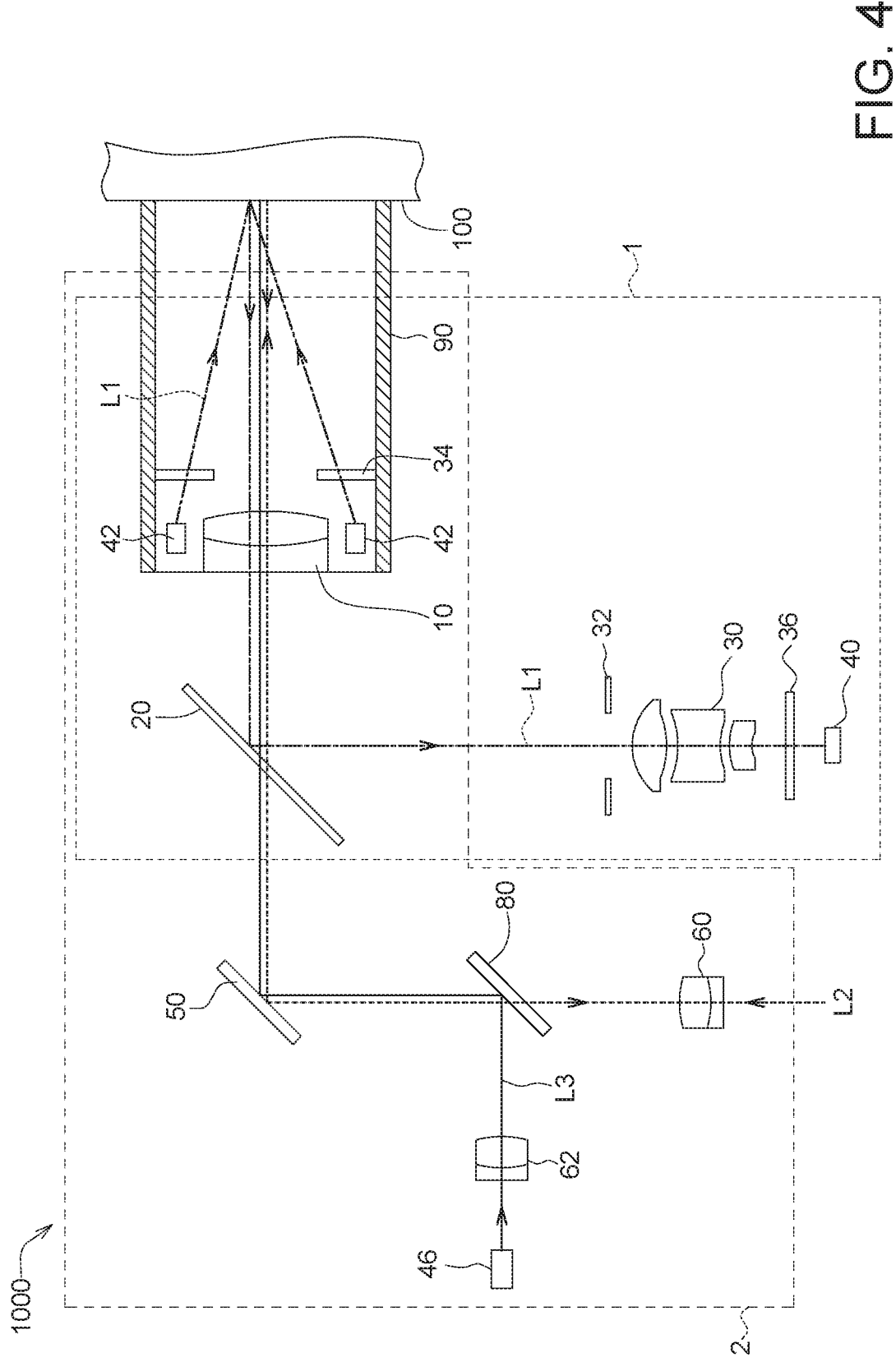
FIG. 4 is a schematic diagram of an optical probe for detecting a biological tissue according to an exemplary embodiment of the disclosure.

However, in other embodiments, the first optical mirror 20 may reflect the first detecting light L1 and may be penetrated by the second detecting light L2. As shown in FIG. 4, the scanner 50 is disposed at one side of the first optical mirror 20 opposite to the telecentric lens 10, and the lens assembly 30 is disposed in the projection position of the first optical mirror 20. In detail, the first optical mirror 20 can be designed to allow a light with a wavelength ranging from 700 nm to 900 nm passing through, and reflect a light with a wavelength ranging from 300 nm to 700 nm. Therefore, the wavelength corresponding to the first detecting light L1 will range from 300 nm to 700 nm, and the wavelength corresponding to the second detecting light L2 will range from 700 nm to 900 nm.

The first optical mirror 20 may be fixed or movable. If the first optical mirror 20 is fixed, the optical probe 1000 for detecting the biological tissue 100 may capture the surface image and the tomography image at the same time. However, if the first optical mirror 20 is movable, the optical probe 1000 for detecting the biological tissue 100 may capture the surface image and the tomography image individually or in company. In the embodiment of FIG. 2, when the movable first optical mirror 20 is removed, the surface imaging module 1 may capture the surface image alone, while in the embodiment of FIG. 4, when the movable first optical mirror 20 is removed, the tomography capturing module 2 may capture the tomography image alone.

Please refer to FIG. 2, FIG. 3, and FIG. 4. In the embodiments of FIG. 2 and FIG. 4, the optical probe 1000 for detecting a biological tissue 100 further comprises an aperture 32. The aperture 32 is disposed between the telecentric lens 10 and the lens assembly 30, and located in a position less than 0.56 times of a back focal length BFL of the telecentric lens 10 from the back focal plane BFS of the telecentric lens 10 to the biological tissue 100. In detail, there is a surface S in the position of 0.56 times of the back focal length BFL of the telecentric lens 10 from the back focal plane BFS of the telecentric lens 10 to the biological tissue 100, and the aperture 32 is disposed between the surface S and the back focal length BFL of the telecentric lens 10. Therefore, it may increase a resolution of the optical probe 1000 for detecting a biological tissue 100, decrease a volume of the surface imaging module 1, and provide good efficiency of light collection. It is noted that the position of the aperture 32 needs to be carefully designed. If the position of the aperture 32 is in a position more than 0.56 times of the back focal length BFL of the telecentric lens 10 (that is the surface S toward the telecentric lens 10), an area between the aperture 32 and the telecentric lens 10 may be too small to dispose the first optical mirror 20. If the position of the aperture 32 is in the back focal length BFL of the telecentric lens 10 toward the imaging sensor 40, an edge of images will be darker to cause vignetting. Besides, in the embodiment of FIG. 2, the aperture 32 may be combined and disposed inside the lens assembly 30. In the embodiment of FIG. 3, the aperture 32 may be disposed between the first optical mirror 20 and the lens assembly 30.

In one embodiment, a f-number of the surface imaging module 1 near the imaging sensor 40 ranges from 2 to 5. If the f-number is more than the range from 2 to 5, the request of the diameter of the lens assembly 30 will increase. This will not facilitate the reduction of the optical probe 1000 for detecting the biological tissue 100. Moreover, it may cause the imaging sensor 40 to underexpose. When the f-number is less than the range from 2 to 5, an aberration between the telecentric lens 10 and the lens assembly 30 will increase, and this also increase the complexity of overall optical structures. In addition, a size of the imaging sensor 40 is smaller than a field of vision (FOV) of the surface imaging module 1.

Figure 5:
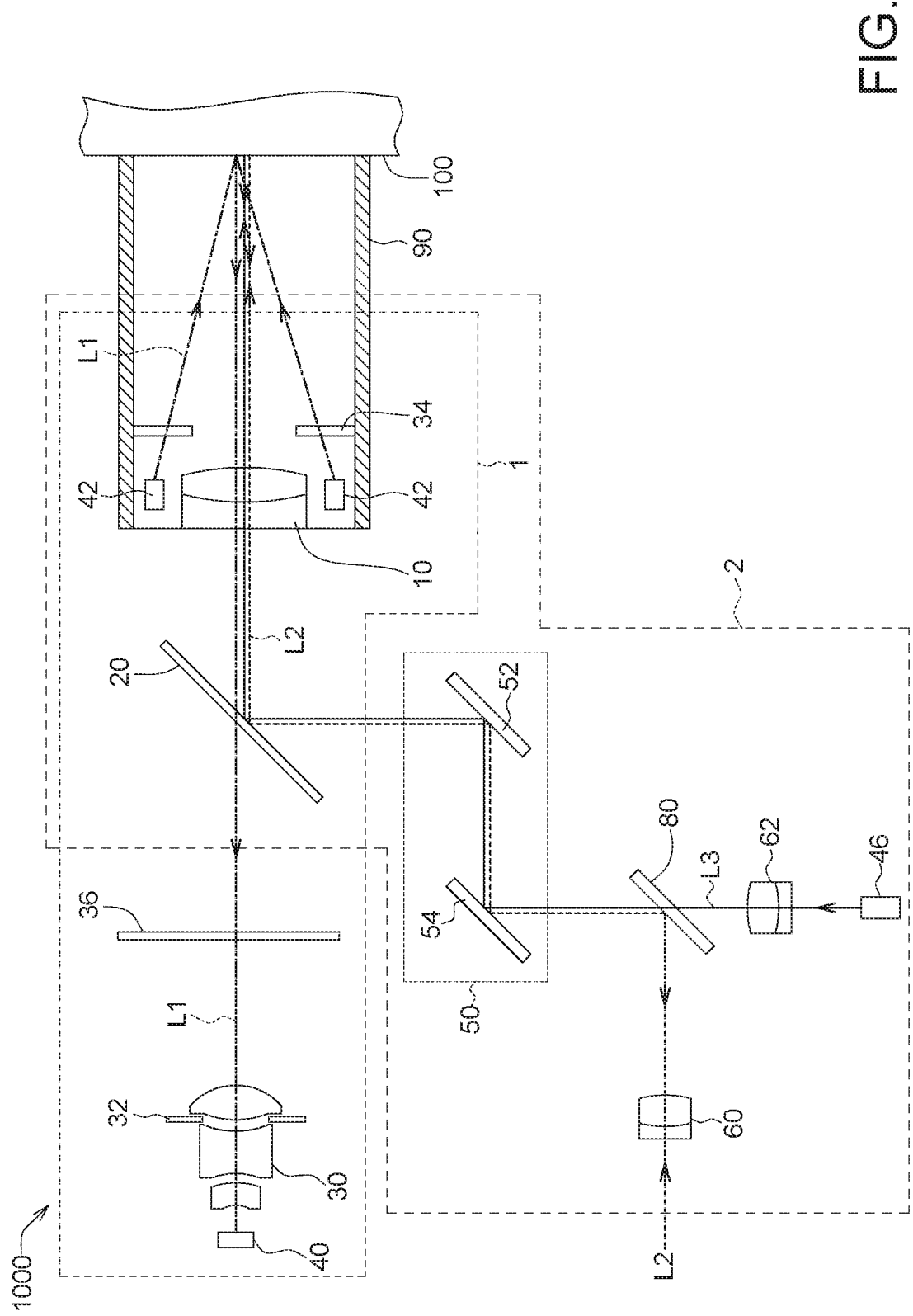
FIG. 5 is a schematic diagram of an optical probe for detecting a biological tissue according to an exemplary embodiment of the disclosure.

Please refer to FIG. 2, FIG. 4, and FIG. 5. In one embodiment, the light source 42 is disposed around the telecentric lens 10, to have the first detecting light L1 being emitted to the biological tissue 100, and then transmitted to the imaging sensor 40 via the first optical path. The optical probe 1000 for detecting the biological tissue 100 further comprises a first polarizer 34 and a second polarizer 36. The first polarizer 34 has a hollow ring shape and is disposed between the light source 42 and the biological tissue 100 without covering the second optical path, and the second polarizer 36 is disposed between the telecentric lens 10 and the imaging sensor 40. It is noted that the second polarizer 36 may be set in any place between the telecentric lens 10 and the imaging sensor 40. Take the embodiment of FIG. 4 as an example, the second polarizer 36 is disposed between the lens assembly 30 and the imaging sensor 40. However, in the embodiment of FIG. 5, the second polarizer 36 is disposed between the lens assembly 30 and the first optical mirror 20, but the scope of the disclosure is not limited thereto. The first polarizer 34 and the second polarizer 36 may decrease a reflection of the biological tissue 100. In one embodiment, optical axes of the first polarizer 34 and the second polarizer 36 may be vertical or caused an angle. As long as polarization directions of the first polarizer 34 and the second polarizer 36 are different, the first polarizer 34 and the second polarizer 36 are workable in this case, but the scope of the disclosure is not limited thereto. In addition, the light source 42 may be an LED, a color adjustable LED, or an UV LED to detect different type of states of the biological tissue 100. For example, using skin as the biological tissue 100, textures and freckles of the skin can be observed by using different wavelengths of the light source 42, and a stimulated fluorescence of bacteria on the surface of the skin can be observed by using UV LED as the light source 42. When the optical probe 1000 for detecting the biological tissue 100 detects in company with the first polarizer 34 and the second polarizer 36, if a parallel polarized light is produced, it may increase a contrast ratio of the textures of the skin surface, and if a cross polarized light is produced, it may obtain distributions of blood vessels and melanin beneath the skin surface.

In one embodiment, a field of vision of the tomography capturing module 2 ranges from 2 to 5 mm to observe larger ranges of the biological tissue 100. In other embodiment, the field of vision of the tomography capturing module 2 may equal to the field of vision of the surface imaging module 1 to detect the surface condition and the deep structure at the same location. Take detecting skin as an example, the same field of vision of the surface imaging module 1 and the tomography capturing module 2 may detect the surface condition and the deep structure of skin at the same location.

Besides, a f-number of the tomography capturing module 2 near the biological tissue 100 ranges from 5.8 to 8.75. It is noted that if the f-number is greater than the range from 5.8 to 8.75, it may cause an insufficient horizontal resolution of the biological tissue 100, and if the f-number is less than the range from 5.8 to 8.75, it may increase the aberration of the telecentric lens 10 so as to increase the complexity of overall optical structures and will not facilitate the reduction of the optical probe 1000 for detecting the biological tissue 100.

The scanner 50 may transform the second detecting light L2 with single angle to a multi-angle collimated light beam. In one embodiment, the scanner 50 may include one or more scan mirrors to perform a scanning process, wherein the scan mirror is a Galvo mirror. Please refer to FIG. 2 and FIG. 4. The scanner 50 includes a scan mirror located on the back focal plane BFS of the telecentric lens 10 to perform a linear scanning process. In the embodiment of FIG. 5, the scanner 50 includes a first scan mirror 52 and a second mirror 54, the position of the back focal plane BFS of the telecentric lens 10 is located between the first scan mirror 52 and the second mirror 54, and the first scan mirror 52 and the second mirror 54 may perform a plane scanning process.

In one embodiment, the first collimator 60 may collimate the second detecting light L2 emitted from the optical fiber coupler 3000 to incident to the scanner 50. Please refer to FIG. 4 and FIG. 5. The optical probe 1000 for detecting the biological tissue 100 further comprises a second collimator 62, a second optical mirror 80 and a scanning indicating light 46. The second collimator 62 collimates a scanning indicating light beam L3 emitted from the scanning indicating light 46, and the second optical mirror 80 guides the second detecting light L2 and the scanning indicating light beam L3 which are collimated to pass via the second optical path and a third optical path, respectively. The scanning indicating light beam L3 passes via the third optical path to the biological tissue 100 through the second collimator 62, the second optical mirror 80, the scanner 50, the first optical mirror 20, and the telecentric lens 10. In general, the second detecting light L2 received by the tomography capturing module 2 is an invisible light, so an user cannot directly know the status that the second detecting light L2 irradiates the biological tissue 100. Therefore, by using the scanning indicating light beam L3 as an auxiliary light to indicate a scan position, a capturing position of the biological tissue 100 can be confirmed. In detail, the scanning indicating light 46 is a red laser, but the scope of the disclosure is not limited thereto. The second detecting light L2 received by the tomography capturing module 2 and collimated by the first collimator 60 enters the second optical mirror 80 in a direction different from an incident direction of the scanning indicating light beam L3 collimated by the second collimator 62. After that, from the second optical mirror 80 to the biological tissue 100, the second optical path which the second detecting light L2 passes through almost coincide with the third optical path which the scanning indicating light beam L3 passes through, so that if a red light of the scanning indicating light beam L3 irradiates a position of the biological tissue 100, the position of the biological tissue 100 will be regarded as a position that the second detecting light L2 irradiates.

The second optical mirror 80 guides the second detecting light L2 and the scanning indicating light beam L3 passing through. The second optical mirror 80 may be a dichroic mirror to allow an incident light with a specific wavelength range passing through and reflect another incident light with other wavelength ranges. In the embodiment of FIG. 4, the second optical mirror 80 can be penetrated by the second detecting light L2 and reflect the scanning indicating light beam L3. In detail, the second optical mirror 80 may be designed to allow a light with a wavelength range over 780 nm passing through, and reflect a light with a wavelength ranging under 700 nm. Therefore, it is used the light with the wavelength ranging from 800 nm to 900 nm as the second detecting light L2 and the light with the wavelength ranging from 620 nm to 700 nm as the scanning indicating light beam L3. However, in other embodiments, the second optical mirror 80 may reflect the second detecting light L2 and be penetrated by the scanning indicating light beam L3. As shown in FIG. 5, the second optical mirror 80 can be designed to allow a light with a wavelength range under 700 nm passing through, and reflect a light with a wavelength range over 780 nm. Therefore, the light with the wavelength ranging from 800 nm to 900 nm is used as the second detecting light L2 and the light with the wavelength ranging from 620 nm to 700 nm is used as the scanning indicating light beam L3. Besides, the scanning indicating light beam L3 also passes through the first optical mirror 20, so it may be designed that a wavelength in 50% transmittance of the first optical mirror 20 is within a range of a central wavelength of the scanning indicating light beam L3. For example, the red laser is used as the scanning indicating light 46, the range of the central wavelength of the red laser is about 620 nm to 700 nm, so it may choose a material that the wavelength in 50% transmittance is within the range from 620 nm to 700 nm to make the first optical mirror 20.

Besides, in the embodiments of FIG. 4 and FIG. 5, the optical probe 1000 for detecting the biological tissue 100 further comprises a transparent cover 90, wherein the transparent cover 90 connects to the telecentric lens 10 and a length L of the transparent cover is equal to the front focal length FFL of the telecentric lens 10 to make sure that the biological tissue 100 is fixed on the front focal plane FFS of the telecentric lens 10 and avoid defocusing that causes blurred images.

As aforementioned, by sharing the telecentric lens and the first optical mirror, the optical probe for detecting the biological tissue in the disclosure may have that two different optical paths are in a single probe being realized, so that the optical probe for detecting the biological tissue may detect the skin layer and the deep layer status at the same time.

It will be apparent to those skilled in the art that various modifications and variations can be made to the disclosed embodiments. It is intended that the specification and examples be considered as exemplars only, with a true scape of the disclosure being indicated by the following claims and their equivalents.

What is claimed is:

1. An optical probe for detecting a biological tissue, comprising:
   a surface imaging module, capturing and imaging a surface image of the biological tissue, wherein the surface imaging module includes a telecentric lens, a first optical mirror, a lens assembly, an imaging sensor, and a light source emitting a first detecting light;
   a tomography capturing module, capturing a tomography image of the biological tissue and receiving a second detecting light, wherein the tomography capturing module includes the telecentric lens, the first optical mirror, a scanner, and a first collimator;
   a first polarizer; and
   a second polarizer,
   wherein the first detecting light passes via a first optical path in the following sequence from the light source, through the biological tissue, the telecentric lens, the first optical mirror, the lens assembly, to the imaging sensor, and the second detecting light passes via a second optical path in the following sequence from the first collimator, through the scanner, the first optical mirror, the telecentric lens, the biological tissue, the telecentric lens, the first optical mirror, the scanner, to the first collimator,
   wherein the light source has a light emitting-surface for emitting the first detecting light directly toward the biological tissue,
   wherein the surface imaging module and the tomography capturing module are connected by the telecentric lens in the first optical path and the second optical path,
   wherein the light source is disposed adjacent to the telecentric lens, to have the first detecting light being emitted to the biological tissue, and transmitted to the imaging sensor via the first optical path,
   wherein the first polarizer has a hollow ring shape and is disposed between the light source and the biological tissue, and the second polarizer is disposed between the telecentric lens and the imaging sensor.

2. The optical probe for detecting the biological tissue as claimed in claim 1, wherein a focal length of the telecentric lens ranges from 25 mm to 40 mm, and the biological tissue is located on a front focal plane of the telecentric lens.

3. The optical probe for detecting the biological tissue as claimed in claim 1, wherein a focal length of the telecentric lens is longer than a focal length of the lens assembly.

4. The optical probe for detecting the biological tissue as claimed in claim 3, wherein a ratio of the focal length of the telecentric lens to the focal length of the lens assembly ranges from 1.4 to 2.8.

5. The optical probe for detecting the biological tissue as claimed in claim 1, wherein the first optical mirror has the first detecting light penetrating and has the second detecting light being reflected.

6. The optical probe for detecting the biological tissue as claimed in claim 1, wherein the first optical mirror has the first detecting light being reflected and has the second detecting light penetrating.

7. The optical probe for detecting the biological tissue as claimed in claim 1, further comprising an aperture disposed between the telecentric lens and the lens assembly, and located in a position less than 0.56 times of a back focal length of the telecentric lens from the back focal plane of the telecentric lens to the biological tissue.

8. The optical probe for detecting the biological tissue as claimed in claim 1, wherein a f-number of the surface imaging module near the imaging sensor ranges from 2 to 5.

9. The optical probe for detecting the biological tissue as claimed in claim 1, wherein a size of the imaging sensor is smaller than a field of vision of the surface imaging module.

10. The optical probe for detecting the biological tissue as claimed in claim 1, wherein a field of vision of the tomography capturing module ranges from 5 mm to 10 mm.

11. The optical probe for detecting the biological tissue as claimed in claim 1, wherein a f-number of the tomography capturing module near the biological tissue ranges from 5.8 to 8.75.

12. The optical probe for detecting the biological tissue as claimed in claim 1, wherein the scanner includes a scan mirror located on a back focal plane of the telecentric lens to perform a linear scanning process.

13. The optical probe for detecting the biological tissue as claimed in claim 1, wherein the scanner includes a first scan mirror and a second mirror, a back focal plane of the telecentric lens is located between the first scan mirror and the second mirror, and the first scan mirror and the second mirror performs a plane scanning process.

14. The optical probe for detecting the biological tissue as claimed in claim 1, further comprising a second collimator, a second optical mirror and a scanning indicating light; wherein the second collimator collimates a scanning indicating light beam emitted from the scanning indicating light, and the second optical mirror guides the second detecting light and the scanning indicating light beam which are collimated to pass via the second optical path and a third optical path, respectively;
wherein the scanning indicating light beam passes via the third light path to the biological tissue through the second collimator, the second optical mirror, the scanner, the first optical mirror, and the telecentric lens.

15. The optical probe for detecting the biological tissue as claimed in claim 14, wherein the second optical mirror has the second detecting light penetrating and has the scanning indicating light beam being reflected.

16. The optical probe for detecting the biological tissue as claimed in claim 14, wherein the second optical mirror has the second detecting light being reflected and has the scanning indicating light beam penetrating.

17. The optical probe for detecting the biological tissue as claimed in claim 14, wherein a wavelength in 50% transmittance of the first optical mirror is within a range of a central wavelength of the scanning indicating light beam.

18. The optical probe for detecting the biological tissue as claimed in claim 1, further comprising a transparent cover, wherein the transparent cover connects to the telecentric lens and a length of the transparent cover is equal to a front focal length of the telecentric lens.

* * * * *